US010796788B2

(12) United States Patent
Ni et al.

(10) Patent No.: US 10,796,788 B2
(45) Date of Patent: Oct. 6, 2020

(54) STRUCTURAL DETERMINATION OF CARBOHYDRATES USING SPECIAL PROCEDURE AND DATABASE OF MASS SPECTRA

(71) Applicant: ACADEMIA SINICA, Taipei (TW)

(72) Inventors: Chi-Kung Ni, Taipei (TW); Shang-Ting Tsai, New Taipei (TW); Hsu-Chen Hsu, Yunlin County (TW); Chia-Yen Liew, Taipei (TW); Shih-Pei Huang, Tainan (TW)

(73) Assignee: Academia Sinica, Taipei (TW)

( * ) Notice: Subject to any disclaimer, the term of this patent is extended or adjusted under 35 U.S.C. 154(b) by 341 days.

(21) Appl. No.: 16/011,079

(22) Filed: Jun. 18, 2018

(65) Prior Publication Data

US 2018/0365387 A1    Dec. 20, 2018

Related U.S. Application Data

(60) Provisional application No. 62/521,632, filed on Jun. 19, 2017.

(51) Int. Cl.
*H01J 49/00* (2006.01)
*G16C 20/20* (2019.01)
(Continued)

(52) U.S. Cl.
CPC ......... *G16C 20/20* (2019.02); *G01N 33/5308* (2013.01); *G16C 20/90* (2019.02);
(Continued)

(58) Field of Classification Search
CPC ........ G16C 20/20; G16C 20/90; G16C 20/70; G01N 33/5308; G01N 2560/00; H01J 49/0036; H01J 49/26; H01J 49/0054
See application file for complete search history.

(56) References Cited

U.S. PATENT DOCUMENTS 8,772,044 B2 * 7/2014 Amano .............. G01N 33/6851
436/95
8,853,621 B2 * 10/2014 Trimpin .................. H01J 49/24
250/282

(Continued)

OTHER PUBLICATIONS

Carolyn R. Bertozzi et al; "Chemical Glycobiology"; Science vol. 291; Mar. 23, 2001; pp. 2357-2364.
(Continued)

*Primary Examiner* — Mohammad K Islam
(74) *Attorney, Agent, or Firm* — Muncy, Geissler, Olds & Lowe, P.C.

(57) ABSTRACT

This invention discloses a method for constructing a set of database of one or more saccharides, a logical procedure for automatic determination of sequential mass spectra, and a method, program and system for determination the structures of oligosaccharides and glycoconjugates by the set of database. In one aspect, the sequential mass spectra measured by the method, program or system of the invention maybe instructed according to the logical procedure automatically or manually determined. By comparing the sequential mass spectra to the set of database, the structure of the carbohydrate comprising linkage position, anomeric configuration, composed monosaccharide and branch location of the carbohydrate sample can be identified. In another aspect, the method, program may be used to control one or more mass spectrometer automatically or manually.

19 Claims, 6 Drawing Sheets

(51) Int. Cl.
*G16C 20/90* (2019.01)
*G01N 33/53* (2006.01)
*G16C 20/70* (2019.01)
*H01J 49/26* (2006.01)

(52) U.S. Cl.
CPC ...... *H01J 49/0036* (2013.01); *G01N 2560/00* (2013.01); *G16C 20/70* (2019.02); *H01J 49/0054* (2013.01); *H01J 49/26* (2013.01)

(56) References Cited

U.S. PATENT DOCUMENTS

| | | | | |
|---|---|---|---|---|
| 9,273,339 | B2* | 3/2016 | Goodlett | G16B 10/00 |
| 9,422,582 | B2* | 8/2016 | Anthony | C12N 15/81 |
| 2008/0167824 | A1 | 7/2008 | Reinhold et al. | |
| 2011/0137570 | A1 | 6/2011 | Lapadula et al. | |
| 2018/0246062 | A1* | 8/2018 | Hofmann | G01N 27/622 |

OTHER PUBLICATIONS

Raymond A. Dwek et al.; "Analysis of Glycoprotein-Associated Oligosaccharides"; Annu. Rev. Biochem. vol. 62; 1993. pp. 65-100.
David Walt et al; "Transforming Glycoscience" National Research Council (US) Committee on Assessing the Importance and Impact of Glycomics and Glycosciences. National Academies Press, Washington, DC, USA 2012; pp. 1-208.
Josesph Zaia; "Mass Spectrometry of Oligosaccharides"; Mass Spectrom. Rev. 23; 2004; pp. 161-227.
D. T. Li et al; "Structural Analysis of Chromophore-labeled Disaccharides and Oligosaccharides by Electrospray Ionization Mass Spectrometry and High-performance Liquid Chromatography/Electrospray Ionization Mass Spectrometry"; J. Mass. Spectrom. 33; 1998; pp. 644-652.
Hsing Ling Cheng et al; "Determination of Linkages of Linear and Branched Oligosaccharides Using Closed-Ring Chromophore Labeling and Negative Ion Trap Mass Spectrometry"; J Am. Soc. Mass Spectrom. 13; 2002; pp. 1322-1330.
David J. Harvey; "Fragmentation of Negative Ions from Carbohydrates: Part 1. Use of Nitrate and Other Anionic Adducts for the Production of Negative Ion Electrospray Spectra from N-linked Carbohydrates"; J. Am. Soc. Mass Spectrom. 16; 2005; pp. 622-630.
David J. Harvey; "Fragmentation of Negative Ions from Carbohydrates: Part 2. Fragmentation of High-Mannose N-Linked Glycans"; J Am. Soc. Mass Spectrom. 16; 2005; pp. 631-646.
David J. Harvey; "Fragmentation of Negative Ions from Carbohydrates: Part 3. Fragmentation of Hybrid and Complex N-Linked Glycans"; J Am. Soc. Mass Spectrom. 16; 2005; pp. 647-659.
Bing Guan et al; "MALDI Linear-Field Reflectron TOF Post-Source Decay Analysis of Underivatized Oligosaccharides: Determination of Glycosidic Linkages and Anomeric Configurations Using Anion Attachment"; J Am. Soc. Mass Spectrom. 19; 2008; pp. 1119-1131.
David J. Harvey, et al "Fragmentation of negative ions from N-linked carbohydrates, Part 4. Fragmentation of complex glycans lacking substitution on the 6-antenna"; J. Mass. Spectrom. 45; 2010; pp. 528-535.
Chiharu Konda et al "Linkage Determination of Linear Oligosaccharides by MSn (n > 2) Collision-Induced Dissociation of Z1 Ions in the Negative Ion Mode"; J. Am. Soc. Mass Spectrom. 25; 2014; pp. 248-257.
Tammy T. Fang et al "Differentiation of the anomeric configuration and ring form of glucosyl-glycolaldehyde anions in the gas phase by mass spectrometry: isomeric discrimination between m/z 221 anions derived from disaccharides and chemical synthesis of m/z 221 standards"; Carbohydr. Res. 342; 2007; pp. 217-235.
Tammy T. Fang et al; "The Stereochemical Dependence of Unimolecular Dissociation of Monosaccharide-Glycolaldehyde Anions in the Gas Phase: A Basis for Assignment of the Stereochemistry and Anomeric Configuration of Monosaccharides in Oligosaccharides by Mass Spectrometry via a Key Discriminatory Product Ion of Disaccharide Fragmentation, m/z 221"; J. Am. Chem. Soc. 129; 2007; pp. 9721-9736.
Chiharu Konda; "Assignment of the Stereochemistry and Anomeric Configuration of Sugars within Oligosaccharides via Overlapping Disaccharide Ladders Using MSn"; J. Am. Soc. Mass Spectrom. 25; 2014; pp. 1441-1450.
Angelina S. Palma et al; "Unravelling Glucan Recognition Systems by Glycome Microarrays Using the DesignerApproach and Mass Spectrometry"; Mol Cell Proteomics. 14; 2015; pp. 974-988.
Angelina S. Palma; "Unravelling glucan recognition systems by glycome microarrays using the designer approach and mass spectrometry"; Supplemental Data Mol Cell Proteomics. 14; 2015; pp. 974-988.
Nelly Viseux; "Structural Assignment of Permethylated Oligosaccharide Subunits Using Sequential Tandem Mass Spectrometry"; Anal. Chem. 70; 1998; pp. 4951-4959.
Sies M. van der Kerk; "Differences in fragmentation behaviour between a- and P-linked derivatized xylobiosides: explanation in terms of sigma conjugation"; Int. J. Mass Spectrom. Ion Processes 134; 1994; pp. 41-54.
Jun Xue; "Determination of linkage position and anomeric configuration in Hex-Fuc disaccharides using electrospray ionization tandem mass spectrometry"; Rapid Commun. Mass Spectrom. 18; 2004; pp. 1947-1955.
Sanford Mendonca; "Incremented Alkyl Derivatives Enhance Collision Induced Glycosidic Bond Cleavage in Mass Spectrometry of Disaccharides"; J. Am. Chem. Soc. Mass Spectrom. 14; 2003; pp. 63-78.
David Ashline; "Congruent Strategies for Carbohydrate Sequencing. 1. Mining Structural Details by MSn"; Anal. Chem. 77; 2005; pp. 6250-6262.
Hailong Zhang et al; "Congruent Strategies for Carbohydrate Sequencing. 2. FragLib: An MSn Spectral Library"; Anal. Chem. 77; 2005; pp. 6263-6270.
Anthony J. Lapadula; "Congruent Strategies for Carbohydrate Sequencing. 3. OSCAR: An Algorithm for Assigning Oligosaccharide Topology from MSn Data"; Anal. Chem. 77; 2005; pp. 6271-6279.
Hsu Chen Hsu et al; "Simple Approach for De Novo Structural Identification of Mannose Trisaccharides"; J. Am. Soc. Mass Spectrom. 29; 2018; pp. 470-480.
Hsu Chen Hsu; "Simple Method for De Novo Structural Determination of Underivatised Glucose Oligosaccharides"; Scientific Reports; 2018; pp. 1-12.
Chia Yen Liew et al., "Linkage and Anomeric Configuration Determination of Glucose by Electrospray Ionization Tandem Mass Spectrometry," 65th ASMS Conference on Mass Spectrometry and Allied Topics, Jun. 4-8, 2017, Indianapolis, Indiana, 1 page.
Shang-Ting Tsai et al., "Does low-energy collision-induced dissociation of lithiated and sodiated carbohydrates always occur at anomeric carbon of the reducing end?," 65th ASMS Conference on Mass Spectrometry and Allied Topics, Jun. 4-8, 2017, Indianapolis, Indiana, 1 page.
Jien-Lian Chen; "Collision-induced dissociation of sodiated glucose and identification of anomeric configuration"; Phys. Chem. Chem. Phys.; 2017; pp. 1-9.

\* cited by examiner ered carbohydrates and glycoconjugates.
STRUCTURAL DETERMINATION OF CARBOHYDRATES USING SPECIAL PROCEDURE AND DATABASE OF MASS SPECTRA

CROSS REFERENCE OF RELATED APPLICATIONS

This non-provisional application claims priority to U.S. provisional patent application Ser. No. 62/521,632 filed on Jun. 19, 2017. This and all other extrinsic materials discussed herein are hereby incorporated by reference in their entirety.

BACKGROUND

Technical Field

This invention relates to the structural identification of carbohydrates, and their derivatives with or without labeling. More particularly, the invention relates to a structural identification of carbohydrates by using a set of database and a logical procedure.

Related Arts

Carbohydrates, including monosaccharides, disaccharides, oligosaccharides, polysaccharides, and glycoconjugates, play important roles in biology processes ranging from molecular recognition and signaling to cellular communication. They are important compounds in the future pharmaceutical industry[1]. However, the structures of carbohydrates and glycolconjugates are very complicated[2]. Development of robust analytical methods for structure determination of carbohydrates remains as a challenge.

Mass spectrometry is widely used in structure determination of carbohydrates due to its analytical versatility and high sensitivity. However, only part of the structures which can be determined by using the current mass spectrometry techniques. In addition, the current mass spectrometers measure the sequential mass spectra (MS$^n$) mass spectra without proper guidance. Many mass spectra which do not provide structural information are measured. It is a waste of sample and time. The situation becomes crucial when the amount of sample is limited, which happens when the carbohydrates are extracted from biological systems[3-6].

Collision induced dissociation (CID) sequential mass spectrometry is one of the major methods in mass spectrometry to determine the structure of carbohydrates. The fragments produced from CID are used to determine the carbohydrate structure. The complete structure determination of carbohydrates includes the identification of monomer unit, the determination of linkage types, anomeric configurations, sequence, and branched locations between monomers. Although some empirical fragmentation patterns from mass spectra were used in the determination of linkage types, the identifications of composed monosaccharide, anomeric configurations, and branched location of carbohydrates remain very difficult in mass spectrometry.

Some anion fragments from the CID of disaccharides were used to identify the structure of linear oligosaccharides[7-19]. However, the drawbacks of this method are that the reducing end of the sample has to be derivatized, anion intensities are usually small and sometime it takes 11 hours to obtain a mass spectra with good signal-to-noise ratio, complicated mass spectrometer is required, the structures of two monomers on the reducing side cannot be determined, and it only applies to linear oligosaccharides.

Some CID spectra of derivatized carbohydrates and permethylated carbohydrates were used to identify the structures[20-26]. However, only part of the structures, i.e., linkage, can be determined. The structures like anomeric configuration, branch location, and identification of composed monosaccharide remain very difficult to be determined.

SUMMARY

This invention herein does not have the drawbacks of the other methods described above. In one aspect of the invention, sequential mass spectra (MS$^n$) measurement is guided by a logical procedure, in which fragment ions which do not provide structural information are not be measured in subsequent MS$^n$ mass spectra.

In one aspect, the invention provides a method for constructing a set of database, this method may include the step of: separating anomeric configurations of a saccharide, and measuring and storing one or a plurality of sequential mass spectra of the separated anomeric configurations of the saccharide.

In some embodiment, the saccharide may include one or a plurality of at least a native monosaccharide, derivatized monosaccharide, labelled monosaccharide, unlabeled monosaccharide, fully methylated monosaccharide, partially methylated monosaccharide, native disaccharide, derivatized disaccharide, labelled disaccharide, unlabeled disaccharide, fully methylated disaccharide, partially methylated disaccharide, native linear trisaccharide, derivatized linear trisaccharide, labelled linear trisaccharide, unlabeled linear trisaccharide, fully methylated linear trisaccharide, partially methylated linear trisaccharide, native branched trisaccharide, derivatized branched trisaccharide, labelled branched trisaccharide, unlabeled branched trisaccharide, fully methylated branched trisaccharide, and a combination thereof.

In some other embodiment, the sequential mass spectra comprise positive ion mode mass spectra, positive ion adduct mass spectra or protonated mass spectra.

In another embodiment, the sequential mass spectra are selected from the group consisting of collision induced dissociation (CID) spectra, higher energy collision dissociation (HCD) spectra, electron capture dissociation (ECD) spectra, in-source fragmentation spectra, multi-photon dissociation spectra, infrared multi-photon dissociation (IRMPD) spectra, laser induced photofragmentation spectra, semi-laser method spectra, and a combination thereof.

In one another embodiment, the step of separating anomeric configurations of the saccharide comprises a step of utilizing gas chromatography (GC), liquid chromatography (LC), high performance liquid chromatography (HPLC), ultra-high performance liquid chromatography (UHPLC), ion mobility, or selective glycosidic bond cleavage of structurally determined carbohydrates and glycoconjugates.

In another aspect, the invention further provides a method for determining a structure of a carbohydrate sample, this method may include: constructing a set of database; constructing a logical procedure comprising a spectrum tree in which each connection point of the spectrum tree is a structural decisive fragment and each terminal point of the spectrum tree is an informative fragment; measuring a sequential mass spectrum of the carbohydrate sample according to the logical procedure, when a first fragment in the sequential mass spectrum is the structural decisive fragment in the logical procedure then measuring a subsequent sequential mass spectrum, and when a second fragment in the sequential mass spectrum is the informative fragment in the logical procedure then stop the measurement, and comparing the measured informative fragments to the set of database to identify the structure of the carbohydrate sample.

In some embodiment, identifying the structure of the carbohydrate sample comprises a least an identification of linkage position of the carbohydrate sample, anomeric configuration of the carbohydrate sample, composed monosaccharide of the carbohydrate sample, branch location of the carbohydrate sample, and a combination thereof.

In some embodiment, the logical procedure comprises the selection of a set of structural decisive fragments and informative fragments according to dissociation mechanisms of carbohydrates.

In some embodiment, the carbohydrate sample is selected from the group consisting of at least a native monosaccharide, derivatized monosaccharide, labelled monosaccharide, unlabeled monosaccharide, fully methylated monosaccharide, partially methylated monosaccharide, native disaccharide, derivatized disaccharide, labelled disaccharide, unlabeled disaccharide, fully methylated disaccharide, partially methylated disaccharide, native linear trisaccharide, derivatized linear trisaccharide, labelled linear trisaccharide, unlabeled linear trisaccharide, fully methylated linear trisaccharide, partially methylated linear trisaccharide, native branched trisaccharide, derivatized branched trisaccharide, labelled branched trisaccharide, unlabeled branched trisaccharide, fully methylated branched trisaccharide, partially methylated branched trisaccharide, native linear polysaccharide, derivatized linear polysaccharide, labelled linear polysaccharide, unlabeled linear polysaccharide, fully methylated linear polysaccharide, partially methylated linear polysaccharide, native branched polysaccharide, derivatized branched polysaccharide, labelled branched polysaccharide, unlabeled branched polysaccharide, fully methylated branched polysaccharide, partially methylated branched polysaccharide, native linear carbohydrate, derivatized linear carbohydrate, labelled linear carbohydrate, unlabeled linear carbohydrate, fully methylated linear carbohydrate, partially methylated linear carbohydrate, native branched carbohydrate, derivatized branched carbohydrate, labelled branched carbohydrate, unlabeled branched carbohydrate, fully methylated branched carbohydrate, partially methylated branched carbohydrate, native linear glycoconjugate, derivatized linear glycoconjugate, labelled linear glycoconjugate, unlabeled linear glycoconjugate, fully methylated linear glycoconjugate, partially methylated linear glycoconjugate, native branched glycoconjugate, derivatized branched glycoconjugate, labelled branched glycoconjugate, unlabeled branched glycoconjugate, fully methylated branched glycoconjugate, partially methylated branched glycoconjugate, and a combination thereof.

In some other embodiment, the sequential mass spectrum comprises positive ion mode mass spectrum, positive ion adduct mass spectrum or protonated mass spectrum.

In some other embodiment, the sequential mass spectrum is selected from the group consisting of collision induced dissociation (CID) spectrum, higher energy collision dissociation (HCD) spectrum, electron capture dissociation (ECD) spectrum, in-source fragmentation spectrum, multiphoton dissociation spectrum, infrared multi-photon dissociation (IRMPD) spectrum, laser induced photofragmentation spectrum, semi-laser method spectrum, and a combination thereof.

In some other aspect, the invention provides a non-transitory computer-readable medium storing one or a plurality of instructions configured to be executed by a computer for determining a structure of a carbohydrate sample. The computer stores a set of database and a logical procedure comprises a spectrum tree in which each connection point of the spectrum tree is a structural decisive fragment and each terminal point of the spectrum tree is an informative fragment. The instructions control the computer to execute a plurality steps comprising: measuring a sequential mass spectrum of the carbohydrate sample according to the logical procedure. When a first fragment in the sequential mass spectrum is a structural decisive fragment in the logical procedure then measuring a subsequent sequential mass spectrum, and when a second fragment in the sequential mass spectrum is an informative fragment in the logical procedure then stop the measurement, and comparing the measured informative fragments to the set of database to identify the structure of the carbohydrate sample.

In some embodiment, the instructions instructs the computer to control one or a plurality of mass spectrometers.

In some other embodiment, the step of measuring the sequential mass spectrum of the carbohydrate sample comprises a step of automatically or manually determining measurement of the subsequent sequential mass spectrum.

In some other embodiment, the step of comparing the measured informative fragments to the set of database comprises a step of automatically or manually matching the sequential mass spectra to the set of database.

In some other aspect, the invention provides a system for determining a structure of a carbohydrate sample. The system comprises at least one mass spectrometer, and at least one computer storing a set of database and a program for determining the structure of the carbohydrate sample. The mass spectrometer is connected to the computer, and the program comprises a logical procedure comprising a spectrum tree in which each connection point of the spectrum tree is a structural decisive fragment and each terminal point of the spectrum tree is an informative fragment. The program controls the computer to execute a plurality steps comprising: measuring a sequential mass spectrum of the carbohydrate sample according to the logical procedure, when a first fragment in the sequential mass spectrum is a structural decisive fragment in the logical procedure then measuring a subsequent sequential mass spectrum, and when a second fragment in the sequential mass spectrum is an informative fragment in the logical procedure then stop the measurement, and comparing the measured informative fragments to the set of database to identify the structure of the carbohydrate sample.

In some embodiment, the computer controls the at least one mass spectrometer.

In some other embodiment, the step of measuring the sequential mass spectrum of the carbohydrate sample comprises a step of automatically or manually determining measurement of the subsequent sequential mass spectrum.

In some other embodiment, the step of comparing the measured informative fragments to the set of database comprises a step of automatically or manually matching the sequential mass spectra to the set of database.

One or part or all of these and other features and advantages of the present invention will become readily apparent to those skilled in this art from the following description wherein there is shown and described one embodiment of this invention, simply by way of illustration of one of the modes best suited to carry out the invention. As it will be realized, the invention is capable of different embodiments, and its several details are capable of modifications in various, obvious aspects all without departing from the invention. Accordingly, the drawings and descriptions will be regarded as illustrative in nature and not as restrictive.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DETAILED DESCRIPTION OF THE INVENTION

The present invention now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

It is to be noted that all directional indications (such as up, down, left, right, front, rear and the like) in the embodiments of the present disclosure are only used for explaining the relative positional relationship, circumstances during its operation, and the like, between the various components in a certain specific posture (as shown in the accompanying drawings). If the specific posture changes, the directional indication will also change accordingly.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

In the embodiments as described below, carbohydrates includes monosaccharides, disaccharides, oligosaccharides, polysaccharides, and glycoconjugates.

Figure 1:
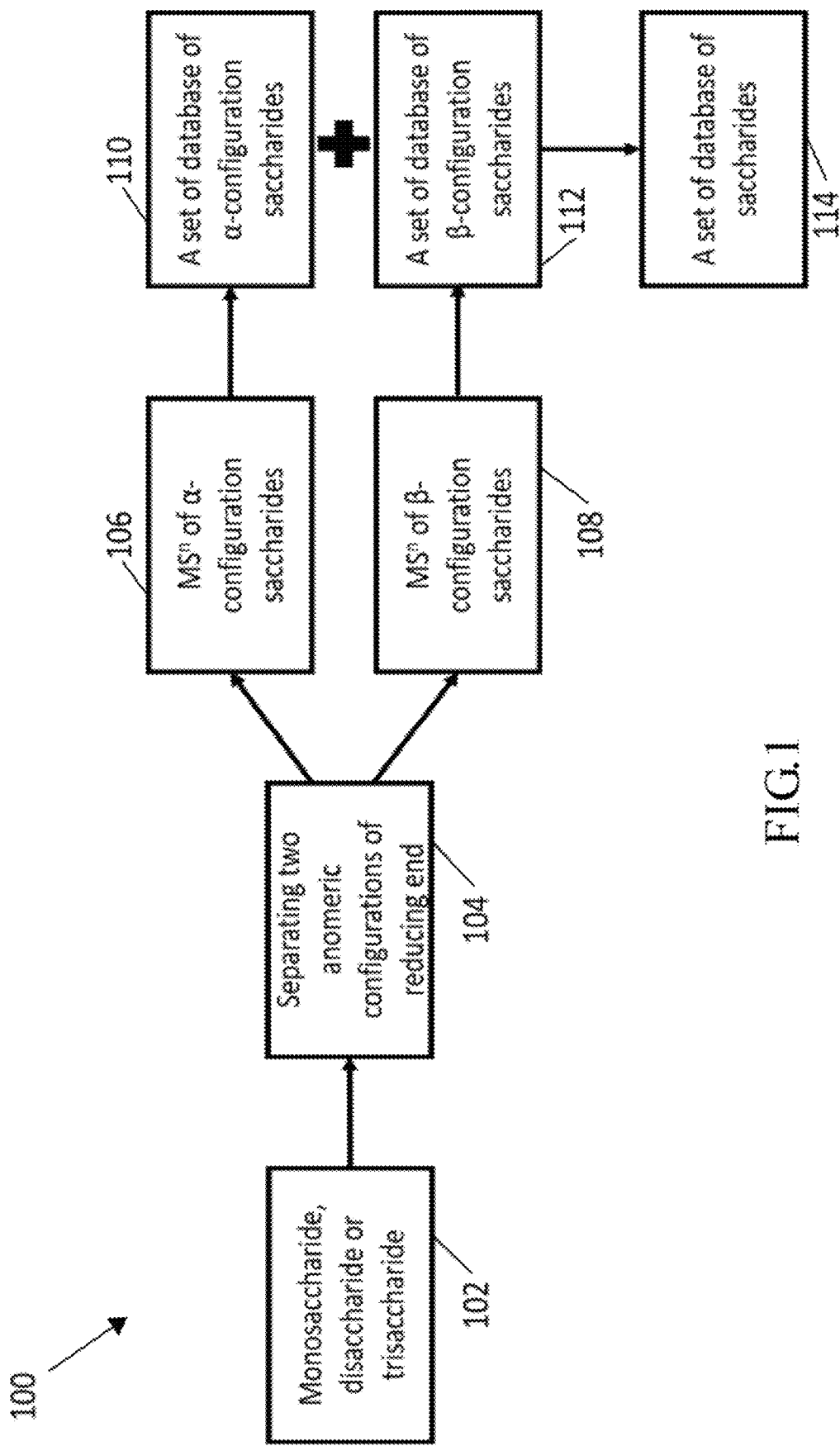
FIG. 1 is a flow chart shows a method for constructing a set of database according to one embodiments of the present invention.
Figure 2:
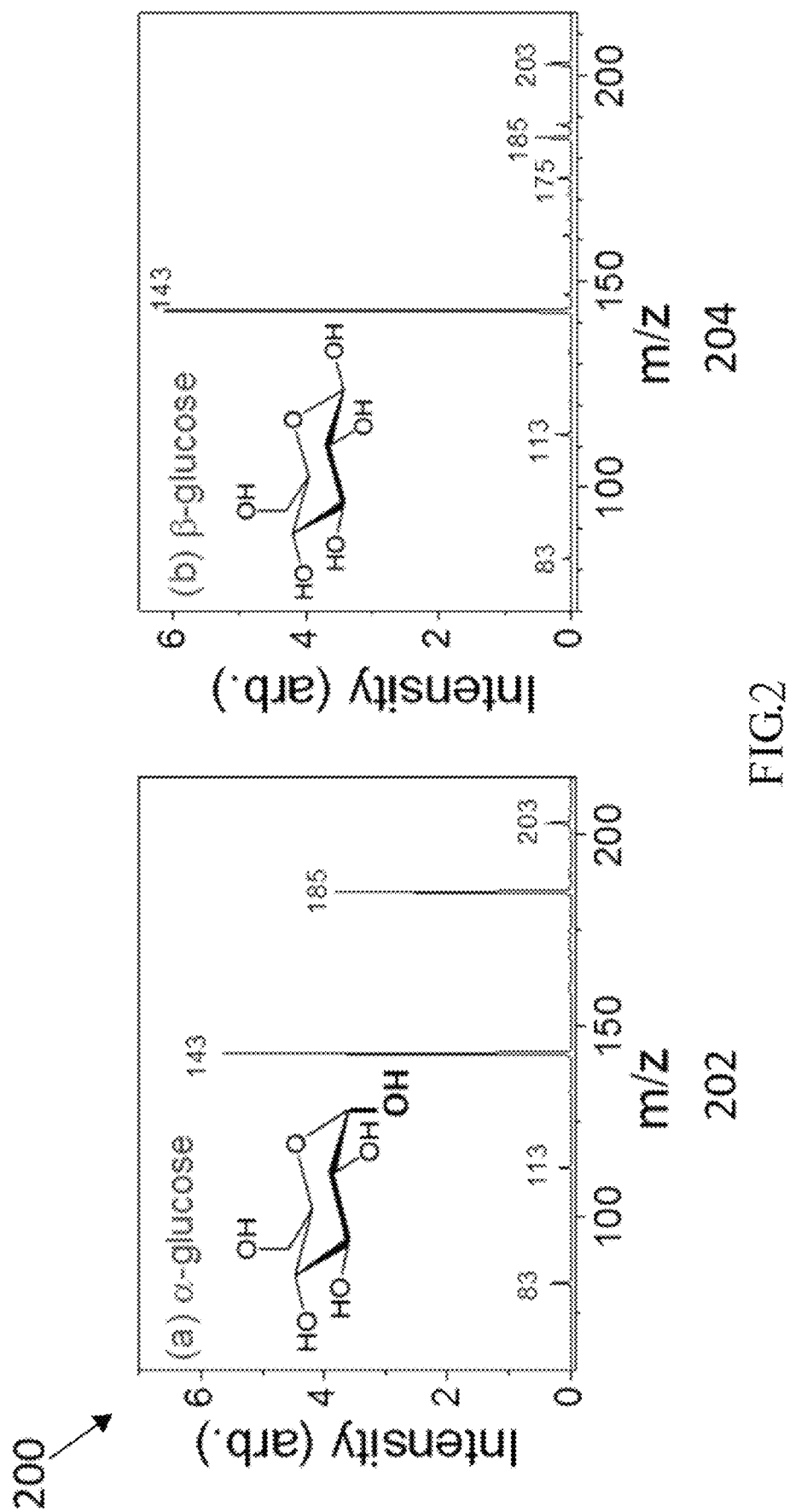
FIG. 2 shows the $MS^2$ CID spectra of two anomeric configurations of glucose of a set of database according to one embodiment of the present invention.
Figure 3:
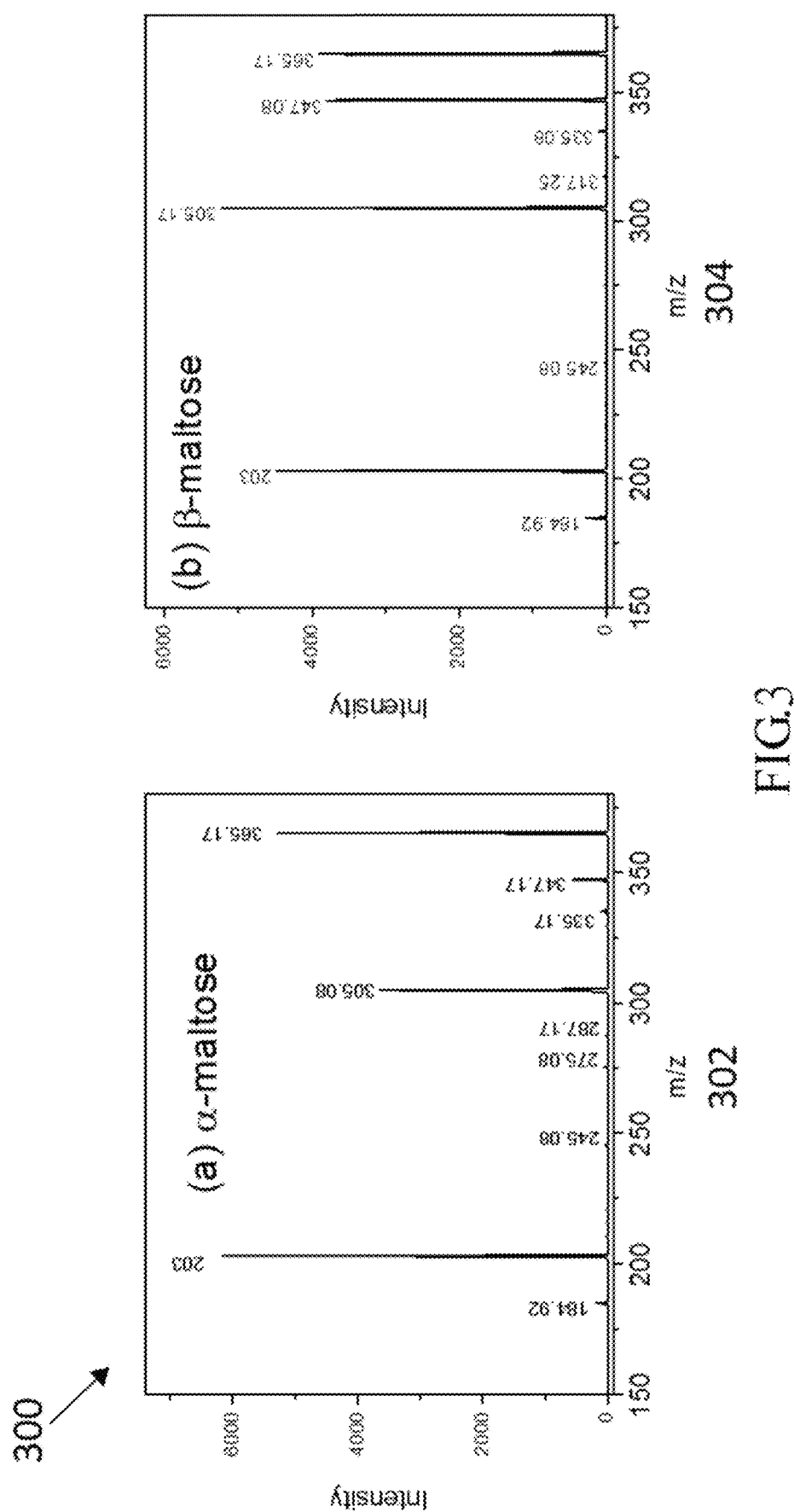
FIG. 3 shows the $MS^2$ CID spectra of two anomeric configurations of maltose of a set of database according to some embodiment of the present invention.
Figure 4:
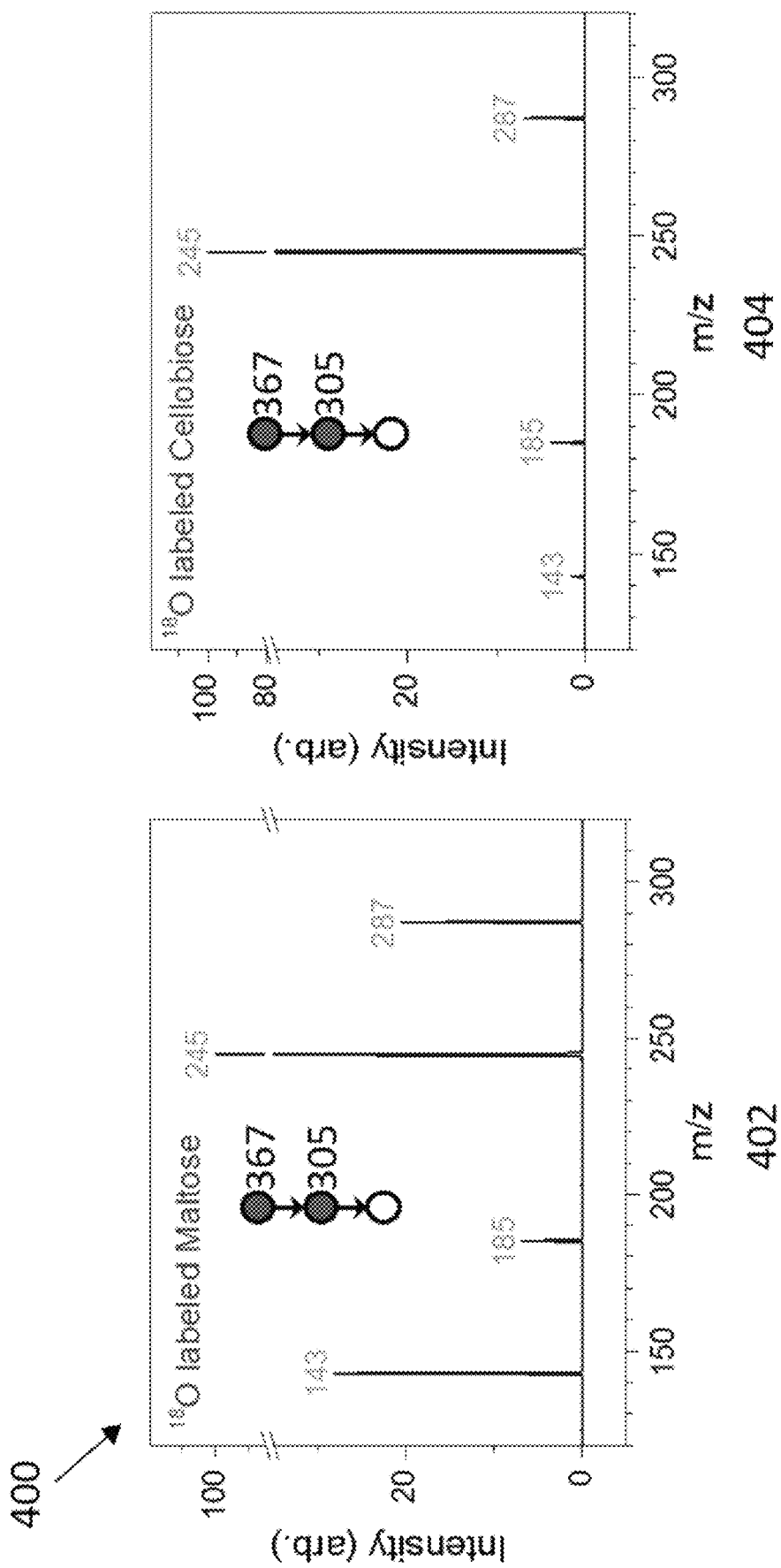
FIG. 4 shows the $MS^3$ CID spectra of two anomeric configurations of maltose of a set of database according to other embodiment of the present invention.

FIG. 1 depicts a method 100 for constructing a set of database 114 according to one embodiment of the invention. The method 100 may include one or more saccharide 102, a step 104 for separating anomeric configurations of the reducing end of saccharide 102, a step 106 for measuring a sequential mass spectra $MS^n$ of the separated α-configurations of the saccharide 102, a step 108 for measuring a sequential mass spectra $MS^n$ of the other separated β-configurations of the saccharide 102. Then the $MS^n$ mass spectra measured from the step 106 may be stored into a set of database 110 of α-configurations of the saccharide 102, and the $MS^n$ mass spectra measured from the step 108 may be stored into a set of database 112 of β-configurations of the saccharide 102. Finally, the set of database 110 and 112 may be combined to construct the set of database 114.

FIGS. 202 and 204 show the $MS^2$ collision induced dissociation (CID) spectra of separated α- and β-configurations of glucose a set of database according to one other embodiment of the invention.

FIGS. 302 and 304 show the $MS^2$ CID spectra of separated α- and β-configurations of maltose a set of database according to one other embodiment of the invention.

FIGS. 402 and 404 show the $MS^3$ CID spectra of separated α- and β-configurations of $^{18}O$ labelled maltose a set of database according to one other embodiment of the invention.

Figure 5:
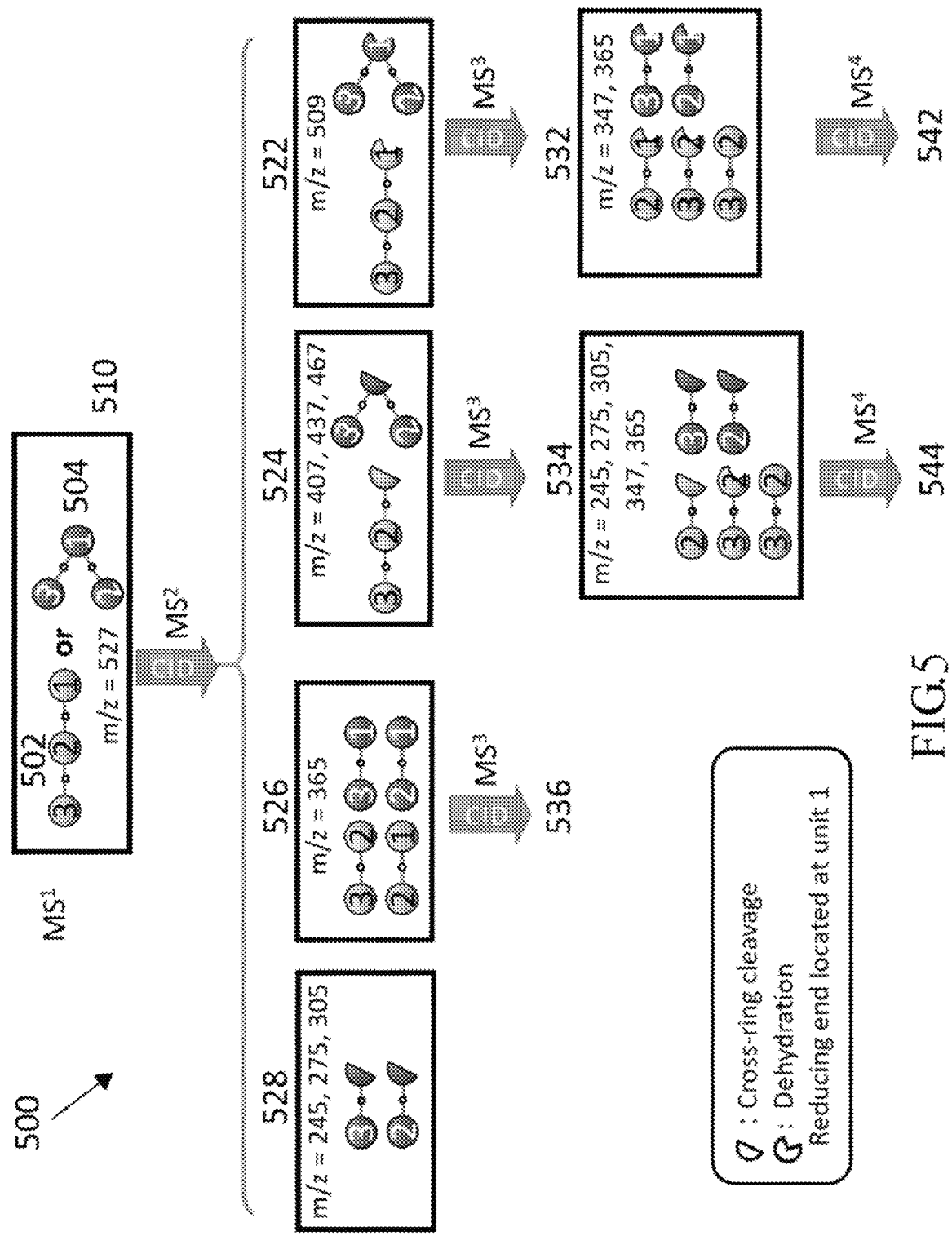
FIG. 5 is a logical procedure for trisaccharides according to one embodiment of the present invention.

In one embodiment of the present invention, FIG. 5 shows a logical procedure for selection of a set of structural decisive fragments and informative fragments according to dissociation mechanisms of carbohydrates. The logical procedure shown in FIG. 5 is provided for trisaccharide. First, there are two possible structural isomers of trisaccharides, one is linear trisaccharide 502, and the other is branched trisaccharide 504. For an unknown carbohydrate sample, since the structure may be linear or branched, the possible fragmentation pathway of linear trisaccharide 502 and branched trisaccharide 504 are considered together. The $MS^2$ structural decisive fragments 522, 524, 526 and 528 are possible $MS^2$ CID fragmentation pathway of linear trisaccharide 502 and branched trisaccharide 504, the $MS^3$ structural decisive fragments 532, 534 and 536 are possible $MS^3$ CID fragmentation pathway from fragments 522, 524 and 526 respectively, and the $MS^4$ structural decisive fragments 542 and 544 are possible $MS^4$ CID fragmentation pathway from fragments 532 and 534 respectively. There are also another possible $MS^2$, $MS^3$, and $MS^4$ fragments of linear trisaccharide 502 and branched trisaccharide 504, however, fragments 510, 522, 524, 526, 532 and 534 in FIG. 5 are structural decisive fragments because these fragments have subsequent mass spectra $MS^{n+1}$, and fragments 528, 536, 542 and 544 are informative fragments because these fragments are terminal fragments. In FIG. 5, fragments 528 do not have to undergo subsequent $MS^3$ fragmentation, so fragments 528 can be used to determine part of the structure of the carbohydrate sample and is denoted as informative fragments 528. In addition, the structural decisive $MS^3$ fragments 536 do not have to undergo subsequent $MS^4$ fragmentation, so fragments 536 can be used to determine part of the structure of the carbohydrate sample and denoted as informative fragments 536. The structural decisive $MS^4$ fragments 542 and 544 do not have to undergo subsequent $MS^5$ fragmentation, so fragments 542 and 544 can be used to determine part of the structure of the carbohydrate sample and denoted as informative fragments 542 and 544. In FIG. 5, the dehydration of a composed monosaccharide denotes loss of water of the composed monosaccharide. In one embodiment of the invention, these informative fragments shown in FIG. 5 are useful to determine the structure of a carbohydrate sample, and also useful to determine the linkage and anomeric configuration on the reducing and non-reducing sides of the carbohydrate sample.

Figure 6:
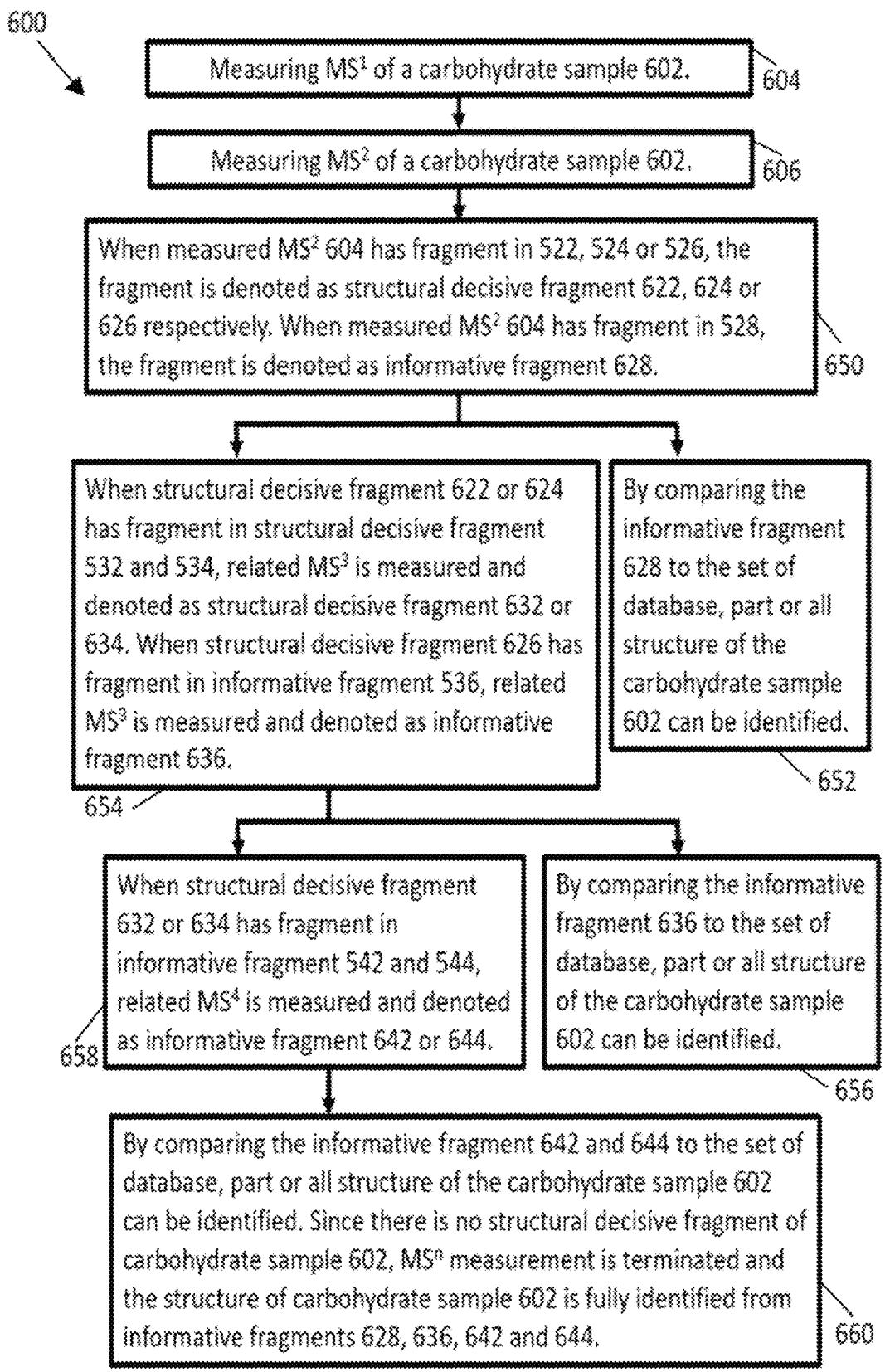
FIG. 6 is a flow chart for identifying the structure of carbohydrates and glycoconjugates by using a logical procedure and a set of database according to one embodiments of the present invention.

In other embodiment of the present invention, FIG. 6 shows a flow chart for identifying the structure of a to-be-determined carbohydrate sample 602 by using the logical procedure 500 and a set of database 114. First, $MS^1$ of carbohydrate sample 602 and $MS^2$ of carbohydrate sample 602 are measured and denoted as 604 and 606. Then, when measured $MS^2$ 604 has fragment in 522, 524 or 526 of the logical procedure 500 shown in FIG. 5, the fragment is denoted as structural decisive fragment 622, 624 or 626 respectively. When measured $MS^2$ 604 has fragment in 528 of the logical procedure 500 shown in FIG. 5, the fragment is denoted as informative fragment 628. Since the fragment 628 is informative fragment, there is no need of subsequent $MS^3$ fragmentation, and, by comparing the informative fragment 628 to the set of database 114, part or all structure of the carbohydrate sample 602 can be identified. When structural decisive fragment 622 or 624 has fragment in structural decisive fragment 532 and 534, related $MS^3$ is measured and denoted as structural decisive fragment 632 or 634. When structural decisive fragment 626 has fragment in informative fragment 536, related $MS^3$ is measured and denoted as informative fragment 636.

Since the fragment 636 is informative fragment, there is no need of subsequent $MS^4$ fragmentation, and, by comparing the informative fragment 636 to the set of database 114, part or all structure of the carbohydrate sample 602 can be identified. When structural decisive fragment 632 or 634 has fragment in informative fragment 542 and 544, related $MS^4$ is measured and denoted as informative fragment 642 or 644. Because the fragments 642 and 644 are informative fragments, there is no need of subsequent $MS^5$ fragmentation. Thus, the measurement of $MS^n$ fragmentation is terminated.

By comparing the informative fragment 642 and 644 to the set of database 114, part or all structure of the carbohydrate sample 602 can be identified. Finally, the structure of carbohydrate sample 602 is fully identified from informative fragments 628, 636, 642 and 644.

One of the embodiments of the present invention is the method to generate a set of database. The method is designed based on the dissociation mechanism of carbohydrates from our high level quantum chemistry calculations and experimental measurement. First, a low-energy dissociation is preferable. The energy for dissociation is controlled such that it is only sufficient for the occurrence of dissociation reactions which have low barrier heights. Cation adducts, such as (but not limited to) sodium ion, lithium ion, proton, $NH_4^+$, $(NH_2)_2H^+$ ion adducts, are preferably used in the process, because they are the most commonly observed ions and have a high ion intensity in typical oligosaccharide mass spectra. Most importantly, they are an efficient energy discriminator due to the loose transition state property of the corresponding dissociation channels. The combination of low-energy dissociation and cation adducts enables the selectivity of specific chemical bond cleavage.

Another embodiments of the present invention is a logical procedure for structural determination of the carbohydrates. The carbohydrates to-be-determined are in situ dissociated into fragments. Only the fragments which are structural decisive are subsequently fragmented to their corresponding fingerprint fragments and compared with the database. The structural decisive fragments are determined according to a logic procedure, another embodiment of the present invention.

The logical procedure to determine the structural decisive fragments for subsequent mass spectrum measurement is based on the findings of our high level quantum chemistry calculations and our recent experimental measurement. (1) The fragmentation patterns of dehydration and cross-ring dissociation can be used directly in linkage determination, but only on the reducing side of carbohydrates. (2) Dehydration is mainly related to the relative position of O1 and O0 atoms of the reducing sugar. Therefore, the anomeric configurations can be determined by the dehydration branching ratio. (3) The dissociation mechanism of glycosidic bond cleavage is analogous to that of dehydration. The logical procedure that helps to determine the structural decisive fragments are completely lack in previous method.

Accordingly, the logical procedure for determining structure of carbohydrates and glycoconjugates can be exemplified by the scheme shown in FIG. 5. In the logical procedure shown in FIG. 5, carbohydrates containing three monosaccharides (i.e., trisaccharides) are used as an example for explain the logical procedure and concept of the method for determining structure of carbohydrates and glycoconjugates.

Moreover, although FIG. 5 presents a logical procedure for identifying the structurally decisive ions of trisaccharides, other similar schemes for carbohydrates containing more than three monosaccharides can be developed using the similar concept.

The logical procedure for the identification of structural decisive fragments comprises the following steps. The first step ($MS^n$) includes the generation of fragment ions (Y and C ions) from carbohydrates in mass spectrometer. These ions are used in the next step to determine the linkage and anomeric configuration on the reducing and non-reducing sides of the oligosaccharides, respectively. The linkage position and branched location of the first glycosidic bond on the reducing side can also be determined using the A ions in the same CID spectrum. The second step is the generation of B, C, Y, and Z ion ions from the A ions produced in $MS^2$. The third step is the measurement of $MS^3$, $MS^4$ and $MS^5$ of these B, C, Y, and Z ions and made the comparison with our database. If necessary, the logical procedure can be repeated for $MS^n$ (n>3). The entire logical procedure can be simplified as the flow chart shown in FIG. 6.

The method and logical procedure according to one embodiment of the present invention can be carried out as computer programs for the automatic or manual measurement and determination of oligosaccharide structures. At first, it is to control the mass spectrometer and automatically determine the $MS^n$ sequence, according to the logical procedure that is built according to one embodiment of the present invention, for mass spectrometer during the measurement. Later, it is to determine the structure of carbohydrates automatically or manually by the comparison of measured mass spectra and our database.

The methods and the logical procedure according to some embodiments of the present invention can be applied for the structural determination of carbohydrates and glycoconjugates that are used in academy and industry.

The foregoing description of the embodiment of the present invention has been presented for purposes of illustration and description. It is not intended to be exhaustive or to limit the invention to the precise form or to exemplary embodiments disclosed. Accordingly, the foregoing description should be regarded as illustrative rather than restrictive. Obviously, many modifications and variations will be apparent to practitioners skilled in this art. The embodiments are chosen and described in order to best explain the principles of the invention and its best mode practical application, thereby to enable persons skilled in the art to understand the invention for various embodiments and with various modifications as are suited to the particular use or implementation contemplated. It is intended that the scope of the invention be defined by the claims appended hereto and their equivalents in which all terms are meant in their broadest reasonable sense unless otherwise indicated. It should be appreciated that variations may be made in the embodiments described by persons skilled in the art without departing from the scope of the present invention as defined by the following claims. Moreover, no element and component in the present disclosure is intended to be dedicated to the public regardless of whether the element or component is explicitly recited in the following claims.

REFERENCES

1. *Science* 291, 2357-2364 (2001).
2. National Research Council (US) Committee on Assessing the Importance and impact of Glycomics and Glycosciences. National Academies Press, Washington, D.C., USA (2012).
3. US Patent 2008/0167824 A1.
4. US Patent 2011/0137570 A1.
5. *Ann. Rev Biochem.* 62, 65-100 (1993).
6. *Mass Spectrom. Rev.* 23, 161-227 (2004).
7. *J. Mass. Spectrom.* 33, 644-652 (1998).
8. *J Am. Soc. Mass Spectrom.* 13, 1322-1330 (2002).
9. *J. Am. Soc. Mass Spectrom.* 16, 622-630 (2005).
10. *J Am. Soc. Mass Spectrom.* 16, 631-646 (2005).
11. *J Am. Soc. Mass Spectrom.* 16, 647-659 (2005).
12. *J Am. Soc. Mass Spectrom.* 19, 1119-1131 (2008).
13. *J. Mass. Spectrom.* 45, 528-535 (2010).
14. *J. Am. Soc. Mass Spectrom.* 25, 248-257 (2014).
15. *Carbohydr. Res.* 342, 217-235 (2007).
16. *J. Am. Chem. Soc.* 129, 9721-9736 (2007).
17. *J. Am. Soc. Mass Spectrom.* 25, 1441-1450 (2014).
18. *Mol Cell* Proteomics. 14, 974-88 (2015).
19. *Mol Cell* Proteomics. 14, 974-88 (2015), Supplemental Data.
20. *Anal. Chem.* 70, 4951-4959 (1998).
21. *Int. J. Mass Spectrom.* Ion Processes 134, 41-54 (1994).
22. *Rapid Commun. Mass Spectrom.* 18, 1947-1955 (2004).
23. *J. Am. Chem. Soc. Mass Spectrom.* 14, 63-78 (2003).
24. *Anal. Chem.* 77, 6250-6262 (2005).
25. *Anal. Chem.* 77, 6263-6270 (2005).
26. *Anal. Chem.* 77, 6271-6279 (2005).

What is claimed is:

1. A method for constructing a set of database, comprising steps of:
    separating anomeric configurations of a saccharide, and
    measuring and storing one or a plurality of sequential mass spectra of the separated anomeric configurations of the saccharide.

2. The method according to claim 1, wherein the saccharide is selected from the group consisting of at least a native monosaccharide, derivatized monosaccharide, labelled monosaccharide, unlabeled monosaccharide, fully methylated monosaccharide, partially methylated monosaccharide, native disaccharide, derivatized disaccharide, labelled disaccharide, unlabeled disaccharide, fully methylated disaccharide, partially methylated disaccharide, native linear trisaccharide, derivatized linear trisaccharide, labelled linear trisaccharide, unlabeled linear trisaccharide, fully methylated linear trisaccharide, partially methylated linear trisaccharide, native branched trisaccharide, derivatized branched trisaccharide, labelled branched trisaccharide, unlabeled branched trisaccharide, fully methylated branched trisaccharide, and a combination thereof.

3. The method according to claim 1, wherein the sequential mass spectra comprise positive ion mode mass spectra, positive ion adduct mass spectra or protonated mass spectra.

4. The method according to claim 1, wherein the sequential mass spectra are selected from the group consisting of collision induced dissociation (CID) spectra, higher energy collision dissociation (HCD) spectra, electron capture dissociation (ECD) spectra, in-source fragmentation spectra, multi-photon dissociation spectra, infrared multi-photon dissociation (IRMPD) spectra, laser induced photofragmentation spectra, semi-laser method spectra, and a combination thereof.

5. The method according to claim 1, wherein the step of separating anomeric configurations of the saccharide comprises a step of utilizing gas chromatography (GC), liquid chromatography (LC), high performance liquid chromatography (HPLC), ultra-high performance liquid chromatography (UHPLC), ion mobility, or selective glycosidic bond cleavage of structurally determined carbohydrates and glycoconjugates.

6. A method for determining a structure of a carbohydrate sample, comprising steps of:
    constructing a set of database;
    constructing a logical procedure comprising a spectrum tree in which each connection point of the spectrum tree is a structural decisive fragment and each terminal point of the spectrum tree is an informative fragment;
    measuring a sequential mass spectrum of the carbohydrate sample according to the logical procedure, when a first fragment in the sequential mass spectrum is the structural decisive fragment in the logical procedure then measuring a subsequent sequential mass spectrum, and when a second fragment in the sequential mass spectrum is the informative fragment in the logical procedure then stop the measurement, and
    comparing the measured informative fragments to the set of database to identify the structure of the carbohydrate sample.

7. The method according to claim 6, wherein identifying the structure of the carbohydrate sample comprises a least an identification of linkage position of the carbohydrate sample, anomeric configuration of the carbohydrate sample, composed monosaccharide of the carbohydrate sample, branch location of the carbohydrate sample, and a combination thereof.

8. The method according to claim 6, wherein the logical procedure comprises the selection of a set of structural decisive fragments and informative fragments according to dissociation mechanisms of carbohydrates.

9. The method according to claim 6, wherein the carbohydrate sample is selected from the group consisting of at least a native monosaccharide, derivatized monosaccharide, labelled monosaccharide, unlabeled monosaccharide, fully methylated monosaccharide, partially methylated monosaccharide, native disaccharide, derivatized disaccharide, labelled disaccharide, unlabeled disaccharide, fully methylated disaccharide, partially methylated disaccharide, native linear trisaccharide, derivatized linear trisaccharide, labelled linear trisaccharide, unlabeled linear trisaccharide, fully methylated linear trisaccharide, partially methylated linear trisaccharide, native branched trisaccharide, derivatized branched trisaccharide, labelled branched trisaccharide, unlabeled branched trisaccharide, fully methylated branched trisaccharide, partially methylated branched trisaccharide, native linear polysaccharide, derivatized linear polysaccharide, labelled linear polysaccharide, unlabeled linear polysaccharide, fully methylated linear polysaccharide, partially methylated linear polysaccharide, native branched polysaccharide, derivatized branched polysaccharide, labelled branched polysaccharide, unlabeled branched polysaccharide, fully methylated branched polysaccharide, partially methylated branched polysaccharide, native linear carbohydrate, derivatized linear carbohydrate, labelled linear carbohydrate, unlabeled linear carbohydrate, fully methylated linear carbohydrate, partially methylated linear carbohydrate, native branched carbohydrate, derivatized branched carbohydrate, labelled branched carbohydrate, unlabeled branched carbohydrate, fully methylated branched carbohydrate, partially methylated branched carbohydrate, native linear glycoconjugate, derivatized linear glycoconjugate, labelled linear glycoconjugate, unlabeled linear glycoconjugate, fully methylated linear glycoconjugate, partially methylated linear glycoconjugate, native branched glycoconjugate, derivatized branched glycoconjugate, labelled branched glycoconjugate, unlabeled branched glycoconjugate, fully methylated branched glycoconjugate, partially methylated branched glycoconjugate, and a combination thereof.

10. The method according to claim 6, wherein the sequential mass spectrum comprises positive ion mode mass spectrum, positive ion adduct mass spectrum or protonated mass spectrum.

11. The method according to claim 6, wherein the sequential mass spectrum is selected from the group consisting of collision induced dissociation (CID) spectrum, higher energy collision dissociation (HCD) spectrum, electron capture dissociation (ECD) spectrum, in-source fragmentation spectrum, multi-photon dissociation spectrum, infrared multi-photon dissociation (IRMPD) spectrum, laser induced photofragmentation spectrum, semi-laser method spectrum, and a combination thereof.

12. A non-transitory computer-readable medium storing one or a plurality of instructions configured to be executed by a computer for determining a structure of a carbohydrate sample, wherein the computer stores a set of database and a logical procedure comprises a spectrum tree in which each connection point of the spectrum tree is a structural decisive fragment and each terminal point of the spectrum tree is an informative fragment, and the instructions control the computer to execute a plurality steps comprising:

measuring a sequential mass spectrum of the carbohydrate sample according to the logical procedure, when a first fragment in the sequential mass spectrum is a structural decisive fragment in the logical procedure then measuring a subsequent sequential mass spectrum, and when a second fragment in the sequential mass spectrum is an informative fragment in the logical procedure then stop the measurement, and comparing the measured informative fragments to the set of database to identify the structure of the carbohydrate sample.

13. The non-transitory computer-readable medium according to claim 12, wherein the instructions instructs the computer to control one or a plurality of mass spectrometers.

14. The non-transitory computer-readable medium according to claim 12, wherein the step of measuring the sequential mass spectrum of the carbohydrate sample comprises a step of automatically or manually determining measurement of the subsequent sequential mass spectrum.

15. The non-transitory computer-readable medium according to claim 12, wherein the step of comparing the measured informative fragments to the set of database comprises a step of automatically or manually matching the sequential mass spectra to the set of database.

16. A system for determining a structure of a carbohydrate sample, comprising:

at least one mass spectrometer;

at least one computer storing a set of database and a program for determining the structure of the carbohydrate sample, wherein the mass spectrometer is connected to the computer, and the program comprises a logical procedure comprising a spectrum tree in which each connection point of the spectrum tree is a structural decisive fragment and each terminal point of the spectrum tree is an informative fragment, and the program controls the computer to execute a plurality steps comprising:

measuring a sequential mass spectrum of the carbohydrate sample according to the logical procedure, when a first fragment in the sequential mass spectrum is a structural decisive fragment in the logical procedure then measuring a subsequent sequential mass spectrum, and when a second fragment in the sequential mass spectrum is an informative fragment in the logical procedure then stop the measurement, and comparing the measured informative fragments to the set of database to identify the structure of the carbohydrate sample.

17. The system according to claim 16, wherein the computer controls the at least one mass spectrometer.

18. The system according to claim 16, wherein the step of measuring the sequential mass spectrum of the carbohydrate sample comprises a step of automatically or manually determining measurement of the subsequent sequential mass spectrum.

19. The system according to claim 16, wherein the step of comparing the measured informative fragments to the set of database comprises a step of automatically or manually matching the sequential mass spectra to the set of database.

* * * * *